(12) United States Patent
Han et al.

(10) Patent No.: US 9,012,241 B2
(45) Date of Patent: Apr. 21, 2015

(54) RAPID DETECTION AND IDENTIFICATION OF ENERGETIC MATERIALS WITH SURFACE ENHANCED RAMAN SPECTROMETRY (SERS)

(75) Inventors: Thomas Yong-Jin Han, Livermore, CA (US); Carlos A. Valdez, San Ramon, CA (US); Tammy Y. Olson, Livermore, CA (US); Sung Ho Kim, Livermore, CA (US); Joe H. Satcher, Jr., Patterson, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 526 days.

(21) Appl. No.: 12/844,778

(22) Filed: Jul. 27, 2010

(65) Prior Publication Data

US 2012/0028372 A1 Feb. 2, 2012

(51) Int. Cl.
*G01N 33/532* (2006.01)
*G01N 33/53* (2006.01)
*G01N 33/543* (2006.01)

(52) U.S. Cl.
CPC .... *G01N 33/54346* (2013.01); *G01N 33/54373* (2013.01)

(58) Field of Classification Search
CPC .................. G01N 33/54373; G01N 33/54346; G01N 2400/18; C08B 37/0012
See application file for complete search history.

(56) References Cited

U.S. PATENT DOCUMENTS

| | | |
|---|---|---|
| 5,866,430 A | 2/1999 | Grow |
| 6,040,191 A | 3/2000 | Grow .......................... 436/172 |
| 7,123,359 B2 | 10/2006 | Armstrong et al. ........... 356/301 |
| 7,151,447 B1 | 12/2006 | Willms et al. ................. 340/540 |
| 7,482,168 B2 | 1/2009 | Sailor et al. |

(Continued)

FOREIGN PATENT DOCUMENTS

| | | | | |
|---|---|---|---|---|
| EP | 1 533 607 | 5/2005 | ............. | G01N 21/65 |
| WO | 00/43754 | 7/2000 | ............. | G01N 21/65 |

(Continued)

OTHER PUBLICATIONS

Wang et al. Synthesis of Oligo(ethylenediamino)-b-cyclodextrin modified gold nanoparticles as a DNA concentrator. Mocecular Pharmaceutics 2007, vol. 2, pp. 189-198.*

(Continued)

*Primary Examiner* — Shafiqul Haq
(74) *Attorney, Agent, or Firm* — Zilka Kotab

(57) ABSTRACT

In one embodiment, a system includes a plurality of metal nanoparticles functionalized with a plurality of organic molecules tethered thereto, wherein the plurality of organic molecules preferentially interact with one or more analytes when placed in proximity therewith. According to another embodiment, a method for detecting analytes includes contacting a fluid having one or more analytes of interest therein with a plurality of metal nanoparticles, each metal nanoparticle having a plurality of organic molecules tethered thereto, and detecting Raman scattering from an analyte of interest from the fluid, the analyte interacting with one or more of the plurality of organic molecules. In another embodiment, a method includes chemically modifying a plurality of cyclodextrin molecules at a primary hydroxyl moiety to create a chemical handle, and tethering the plurality of cyclodextrin molecules to a metal nanoparticle using the chemical handle. Other systems and methods for detecting analytes are also described.

20 Claims, 7 Drawing Sheets

(56) References Cited

U.S. PATENT DOCUMENTS

| | | |
|---|---|---|
| 2004/0234958 A1 | 11/2004 | Smith et al. |
| 2005/0101026 A1 | 5/2005 | Sailor et al. ............. 436/106 |
| 2006/0061762 A1* | 3/2006 | Dwight et al. ............ 356/301 |
| 2008/0083138 A1 | 4/2008 | Lacorazza et al. |

FOREIGN PATENT DOCUMENTS

| | | | |
|---|---|---|---|
| WO | 01/77650 | 10/2001 | ........... C07D 213/53 |
| WO | 2008/092118 | 7/2008 | ............. C01B 33/02 |
| WO | WO2008083138 A1 | 7/2008 | |

OTHER PUBLICATIONS

Liu et al. Cyclodextrin-modified gold nanospheres. Langmuir 2000, vol. 16, pp. 3000-3002.*

Ortea-Caballero et al. Tailoring beta-cyclodextrin for DNA complexation and delivery by homogeneous functionalizaiton at secondary face. Organic letters 2008, vol. 10, No. 22, pp. 5143-5146.*

Alvarez et al. Water soluble platinum and palladium nanoparticles modified with thiolated beta-cyclodextrin. Chem. Commun., 2000, pp. 1151-1152.*

Huang et al., "Facile Synthesis and One-Dimensional Assembly of Cyclodextrin-Capped Gold Nanoparticles and Their Applications in Catalysis and Surface-Enhanced Raman Scattering" © XXXX American Chemical Society, J. Phys. Chem C. XXXX, xxx, 000, Jul. 2, 2009, p. A-G.

Sylvia et al., "Surface-Enhanced Raman Detection of 2, 4-Dinitrotoluene Impurity Vapor as a Marker To Locate Landmines" © 2000 American Chemical Society, Anal. Chem., vol. 72, No. 23, Dec. 1, 2000, 75, p. 5834-5840.

Yardin et al., "Photo-Fenton treatment of TNT contaminated soil extract solutions obtained by soil flushing with cyclodextrin" © 2005 Elsevier Ltd., Chemosphere 62 (2006) 1395-1402 www.elsevier.com/locate/chemosphere.

Perl et al., "Self-Assembled Monolayers of ȧ Cyclodextrin Derivatives on Gold and Their Host—Guest Behavior" © 2009 American Chemical Society, Langmuir 2009, vol. 25, No. 3, p. 1534-1539.

Dasary et al., "Gold Nanoparticle Based Label-Free SERS Probe For Ultrasensitive and Selective Detection of Trinitrotoluene," 2009 American Chemical Society, Journal of American Chemical Society, vol. 131, No. 38, Sep. 8, 2009, pp. 13806-13812.

Harper et al., "Remote Chemical Sensing With Quantum Cascade Lasers," Sensors, and Command, Control, Communications, and Intelligence (C3I) Technologies For Homeland Security and Homeland Defense III, E. M. Carapezza, ed., Proceedings of SPIE, vol. 5403, 2004, pp. 378-386.

Baker et al., "Progress in Plasmonic Engineering of Surface-Enhanced Raman-Scattering Substrates Toward Ultra-Trace Analysis," Anal. Bioanal, Chem., vol. 382, 2005, pp. 1751-1770.

Chang et al., "Nanoporous Membranes With Mixed Nanoclusters for Raman-Based Label-Free Monitoring of Peroxide Compounds," 2009 American Chemical Society, Analytical Chemistry, vol. 81, No. 14, July 15, 2009, pp. 5740-5748.

Calzzani Jr., et al., "Detection of Residual Traces of Explosives by Surface Enhanced Raman Scattering Using Gold Coated Substrates Produced by Nanospheres Imprint Technique," Optics and Photonics in Global Homeland Security IV, Proc. of SPIE, vol. 6945, 2008, pp. 69451O/1-69451O/9.

Bertone et al., "Fingerprinting CBRNE Materials Using Surface-Enhanced Raman Scattering," Chemical, Biological, Radiological, Nuclear, and Explosives (CBRNE) Sensing IX, Proc. of SPIE, vol. 6954, 2008, pp. 69540J/1-69540J/7.

Primera-Pedrozo et al., "Nanotechnology-Based Detection of Explosives and Biological Agents Simulants," 2008, IEEE, IEEE Sensors Journal, vol. 8, No. 6, Jun. 2008, pp. 963-973.

Sylvia et al., "Surface-Enhanced Raman Detection of 2,4-Dinitrotoluene Impurity Vapor As A Marker To Locate Landmines," 2000 American Chemical Society, Analytical Chemistry, vol. 72, No. 23, Dec. 1, 2000, pp. 5834-5840.

Fang et al., "Detection of Explosive Vapour Using Surface-Enhanced Raman Spectroscopy," Springer-Verlag 2009, Applied Physics B; Lasers and Optics, vol. 97, 2009, pp. 723-726.

Spencer et al., "Advances In Landmine Detection Using Surface-Enhanced Raman Spectroscopy," Part of the SPIE Conference on Detection and Remediation Technologies for Mines and Minelike Targets IV, Orlando, Florida, Apr. 1999, SPIE, vol. 3710, pp. 373-379.

Spencer et al., "Surface-Enhanced Raman Spectroscopy For Homeland Defense," Chemical And Biological Point Sensors For Homeland Defense, Proceedings of SPIE, vol. 5269, 2004, pp. 1-8.

Stokes et al., "Raman Spectroscopy of Illicit Substances," Optics and Photonics for Counterterrorism and Crime Fighting III, Proc. of SPIE, vol. 6741, 2007, pp. 67410Q/1-67410Q/8.

Hubner et al., "Surface Enhanced Raman Spectroscopy on Chip," Integrated Optics: Devices, Materials, and Technologies XII, Proc. of SPIE, vol. 6896, 2008, pp. 689614/1-689614/10.

Ko et al., "Porous Substrates for Label-Free Molecular Level Detection of Nonresonant Organic Molecules," 2009 American Chemical Society, vol. 3, No. 1, Dec. 15, 2008, pp. 181-188.

Ko et al., "Nanoparticle-Decorated Nanocanals for Surface-Enhanced Raman Scattering," 2008 Wiley-VCH Verlag GmbH & Co., Small 2008, vol. 4, No. 11, pp. 1980-1984

Janni et al., "SERS Detection of The Nuclear Weapons Explosive Triaminotrinitrobenzene," Vibrational Spectroscopy-Based Sensor Systems, Proceedings of SPIE, vol. 4577, 2002, pp. 230-238.

Ruffin et al., "Innovative Smart Micro Sensors for Army Weaponry Applications," Nanosensors And Microsensors for Bio-Systems 2008, Proc. of SPIE, vol. 6931, pp. 693102/1-693102-12.

De La Cruz-Montoya et al., "Enhanced Raman Spectroscopy of 2,4,6-TNT in Anatase and Rutile Titania Nanocrystals," Optics And Photonics in Global Homeland Security II, Proc. of SPIE, vol. 6203, 2006, pp. 62030X/1-62030X/7.

Gelves et al., "Silver Metal Colloidal Film on A Flexible Polymer Substrate," Sensors, and Command, Control, Commmunications, and Intelligence (C3I) Technologies for Homeland Security and Homeland Defense V, Proc. of SPIE, vol. 6201, 2006, pp. 62012C/1-62012C/9.

Bertone et al., "A Nanoengineered Sensor To Detect Vibrational Modes Of Warfare Agents/Explosives Using Surface-Enhanced Raman Scattering," Sensors, and Command, Control, Communications, and Intelligence(C31) Technologies for Homeland Security and Homeland Defense, Pts 1 and 2, vol. 5403, 2004, pp. 387-394.

Ko et al., "Nanoparticle-Decorated Nanocanals For Surface-Enhanced Raman Scattering," Small, vol. 4, No. 11, 2008, pp. 1980-1984.

Vo-Dinh et al., "Gene Detection and Multispectral Imaging Using SERS Nanoprobes and Nanostructures." Nanotechnology in Biology and Medicine: Methods, Devices, and Applications, 2007, pp. 1-10.

Docherty et al., "Simultaneous Multianalyte Identification Of Molecular Species Involved In Terrorism Using Raman Spectroscopy," IEEE, Sensors Journal, vol. 5, Issue 4, Aug. 2005, pp. 632-640 (abstract only).

* cited by examiner

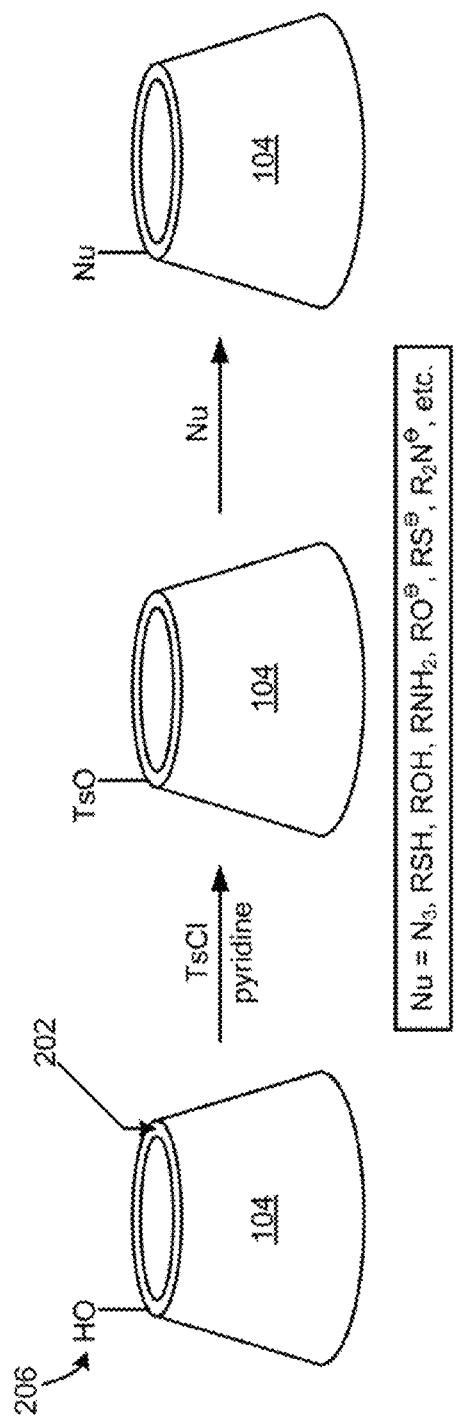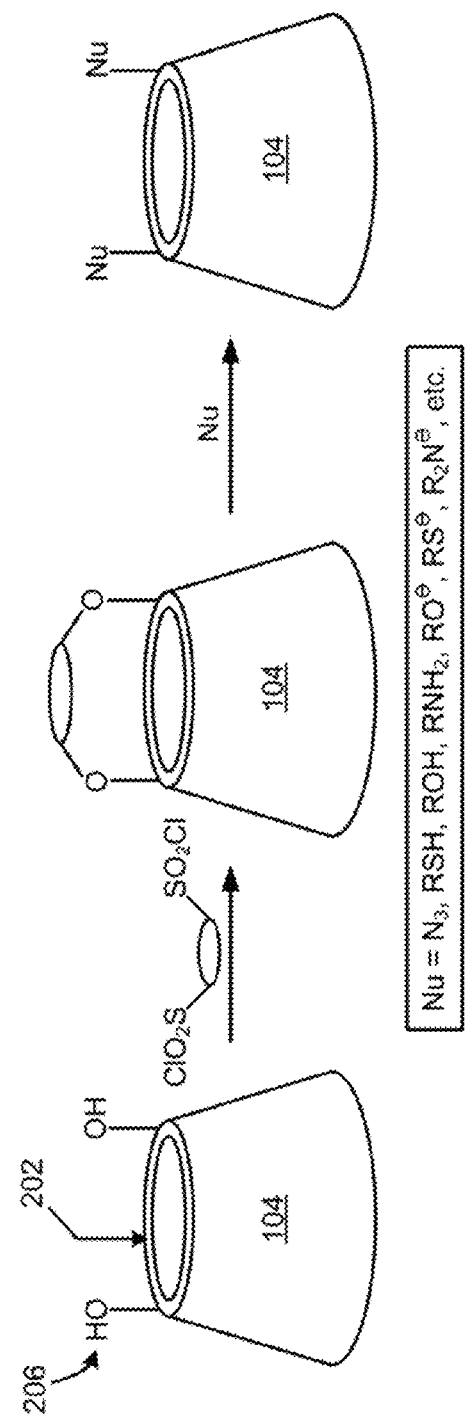
FIG. 3A
FIG. 3B

RAPID DETECTION AND IDENTIFICATION OF ENERGETIC MATERIALS WITH SURFACE ENHANCED RAMAN SPECTROMETRY (SERS)

The United States Government has rights in this invention pursuant to Contract No. DE-AC52-07NA27344 between the United States Department of Energy and Lawrence Livermore National Security, LLC for the operation of Lawrence Livermore National Laboratory.

FIELD OF THE INVENTION

The present invention relates to Surface Enhanced Raman Spectroscopy (SERS), and more particularly, to the rapid detection and identification of energetic materials using SERS.

BACKGROUND

Rapid detection and identification of energetic materials such as explosives is one of the cornerstones of the rapidly evolving war on terrorism, and is used to mitigate emerging terrorist threats around the world, targeting the United States of America and its interests, home and abroad. However, due to the extremely low vapor pressures of many commonly used and available explosives, rapid detection and identification of trace amounts of these explosives using conventional analytical tools are limited. The current state-of-the-art technique for detection and identification of explosive systems is Surface Enhanced Raman Spectroscopy (SERS). SERS utilizes bare, roughened metal surfaces to enhance Raman signals of adsorbed Raman active molecules. The enhancement of the signals can be by as much as $10^{14}$, thus allowing for trace amounts to be detected which could not be detected without the enhancement. However, current use of SERS technology is somewhat limited due to the specificity of the explosives to the substrates (i.e., metal nanoparticles, metal thin films, etc.) used during the collection of explosives. Therefore, a method and system of overcoming the current limitations of SERS technologies to be used in detection and identification of energetic materials would be very beneficial.

SUMMARY

In one embodiment, a system includes a plurality of metal nanoparticles functionalized with a plurality of organic molecules tethered thereto, wherein the plurality of organic molecules preferentially interact with one or more analytes when placed in proximity therewith.

In another embodiment, a method for detecting analytes includes contacting a fluid having one or more analytes of interest therein with a plurality of metal nanoparticles, each metal nanoparticle having a plurality of organic molecules tethered thereto, and detecting Raman scattering from an analyte of interest from the fluid, the analyte interacting with one or more of the plurality of organic molecules.

In yet another embodiment, a method includes chemically modifying a plurality of cyclodextrin molecules at a primary hydroxyl moiety to create a chemical handle, and tethering the plurality of cyclodextrin molecules to a metal nanoparticle using the chemical handle.

Other aspects and embodiments of the present invention will become apparent from the following detailed description, which, when taken in conjunction with the drawings, illustrate by way of example the principles of the invention.

BRIEF DESCRIPTION OF THE DRAWINGS

FIG. 3A shows chemical remodeling of cyclodextrin, according to one embodiment.

FIG. 3B shows chemical remodeling of cyclodextrin, according to one embodiment.

DETAILED DESCRIPTION

Figure 1A:
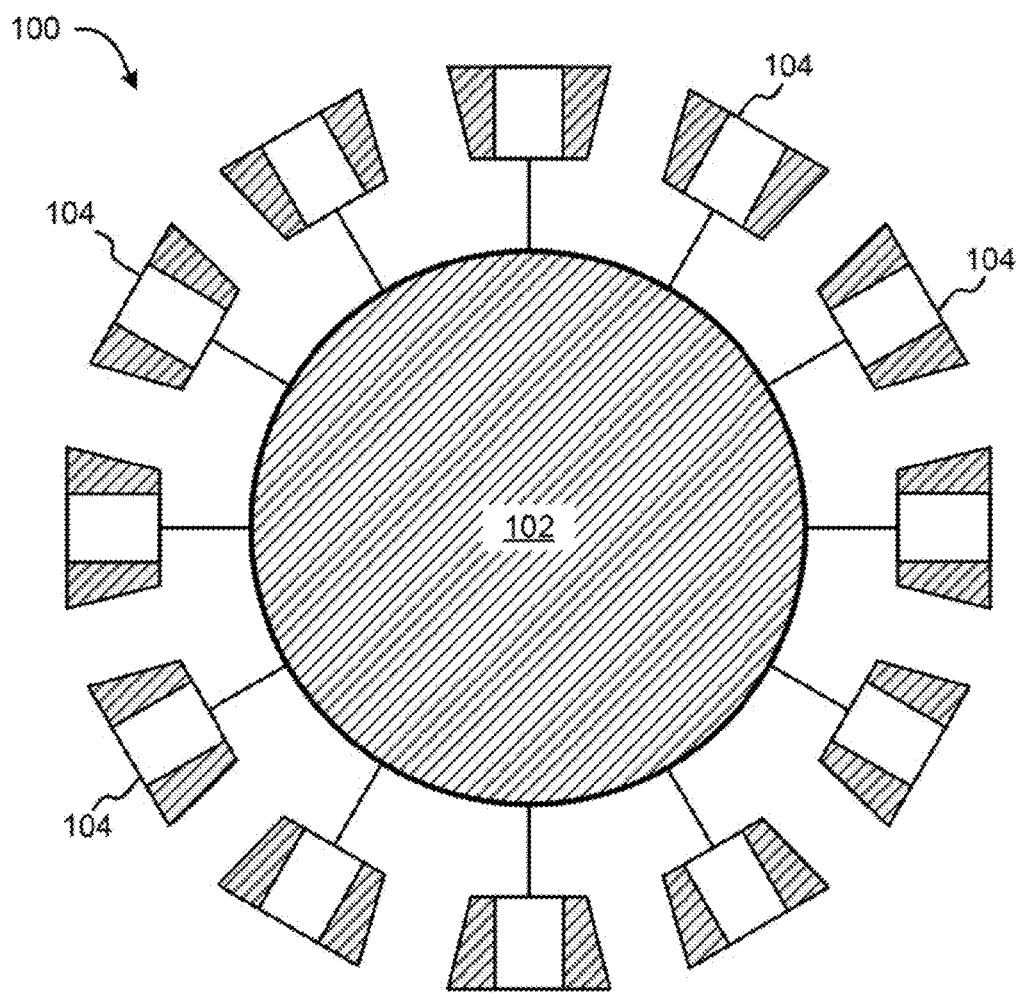
FIG. 1A shows a simplified cross-sectional view of a metal nanoparticle with tethered cyclodextrin molecules, according to one embodiment.

The following description is made for the purpose of illustrating the general principles of the present invention and is not meant to limit the inventive concepts claimed herein. Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and/or as defined in dictionaries, treatises, etc.

It must also be noted that, as used in the specification and the appended claims, the singular forms "a," "an" and "the" include plural referents unless otherwise specified.

In one general embodiment, a system includes a plurality of metal nanoparticles functionalized with a plurality of organic molecules tethered thereto, wherein the plurality of organic molecules preferentially interact with one or more analytes when placed in proximity therewith.

In one general embodiment, a method for detecting analytes includes contacting a fluid having one or more analytes of interest therein with a plurality of metal nanoparticles, each metal nanoparticle having a plurality of organic molecules tethered thereto, and detecting Raman scattering from an analyte of interest from the fluid, the analyte interacting with one or more of the plurality of organic molecules.

In another general embodiment, a method includes chemically modifying a plurality of cyclodextrin molecules at a primary hydroxyl moiety to create a chemical handle, and tethering the plurality of cyclodextrin molecules to a metal nanoparticle using the chemical handle.

According to one embodiment, the current limitations in the use of SERS to detect and identify energetic materials (explosives) can be overcome by functionalizing the substrates used in the SERS techniques with organic molecules specifically designed to bind and retain molecules of explosives, thereby allowing for greater retention of target molecules for rapid detection, while simultaneously lowering the detection limits of explosives generally.

In one approach, a device uses metal nanoparticles functionalized with organic molecules to detect energetic materials. The metal nanoparticles may be one or more of many different types of metals, such as gold, silver, platinum, etc., and preferably possess unique surface properties which enhance the Raman signatures of target molecules on their surface when using Surface Enhanced Raman Spectroscopy (SERS). Particularly applicable in the current context, explosives also cause the metal nanoparticles to exhibit this enhanced Raman signature. The enhanced detection using SERS over contemporary techniques is achieved, in one approach, by tethering specific organic molecules which possess unique properties of binding and retaining energetic materials of interests to the metal nanoparticles, e.g., tethering cyclodextrin to the metal nanoparticles to test for trinitrotoluene (TNT). Having these specific organic molecules on the surfaces of the metal nanoparticles greatly enhances the signals of the target materials (energetic materials or explosives), in addition to lowering detection limits when compared to current technologies, thus allowing for trace amount detection of energetic materials in solution, solid, and/or vapor forms, a clear advantage over conventional techniques.

FIG. 1A shows a simplified cross-sectional schematic diagram of a cyclodextrin (CD) functionalized metal nanoparticle 100, according to one embodiment. Of course, a plurality of CD functionalized (active) metal nanoparticles 100 may be used with SERS for the detection of trace explosives. Since FIG. 1A is only a cross-sectional diagram, the additional CDs 104 tethered to the metal nanoparticle 102 which are not dispersed along the immediate sides of the metal nanoparticle 102 do not appear in this diagram; however, the metal nanoparticles 102 may be covered by tethered CDs 104 along some, most, or all surfaces, and the density of the tethered CDs 104 may be controlled, random, a function of some other factor, etc., according to some approaches. Also, the metal nanoparticles 102 may include, but are not limited to, gold, silver, platinum, etc., and they may be synthesized using techniques as would be known to one of skill in the art. The size ranges of the metal nanoparticles 102 may vary from about 5 nm to about 100 nm without the CDs 104 tethered, in some embodiments. This size range may be a mean diameter, maximum diameter, minimum diameter, median diameter, etc.

Figure 1B:
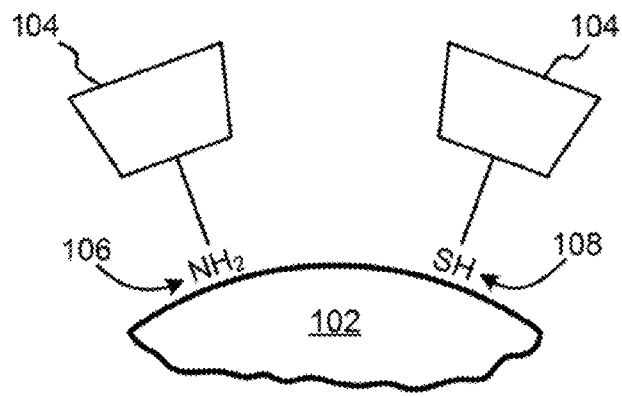
FIG. 1B shows a chemical handle binding a metal nanoparticle to molecules of cyclodextrin, according to one embodiment.

As shown in FIGS. 1A-1B, structurally modified CDs 104 may be tethered to the metal nanoparticles 102 by chemical techniques, as would be known to one of skill in the art. Particularly, primary hydroxyl moieties of the CD 104 may be selectively converted to a thiol functionality 108, an amine functionality 106, etc., thus providing a useful chemical handle for their subsequent attachment to the metal nanoparticles 102, as shown in FIG. 1B.

CDs 104 may also be chemically modified to target specific analytes 110 of interest, in some embodiments. These analytes include, but are not limited to, TNT, tetrahexamine tetranitramine (HMX), cyclotrimethylenetrinitramine (RDX), pentaerythritol tetranitrate (PSTN), 2,4,6-trinitrophenylmethylnitramine (Tetryl), peroxides, and other common explosives.

Figure 2:
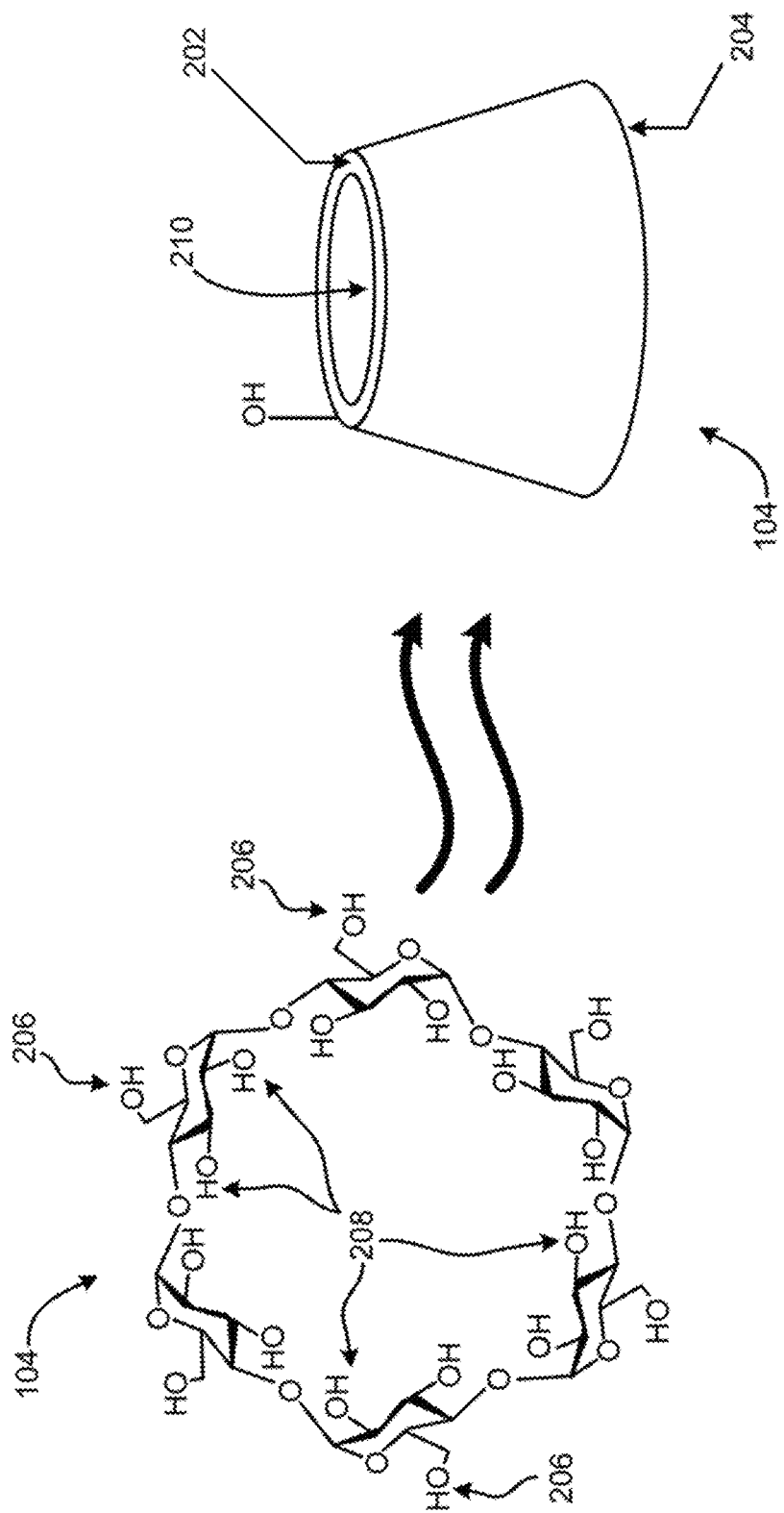
FIG. 2 shows a chemical representation and a stylized representation of cyclodextrin, according to one embodiment.

With regard to modifying a CD 104, it is noted that there are two regions in these toroid-shaped macromolecules that are subject to chemical manipulation, as shown in FIG. 2, according to one embodiment. One region is the primary face 202, which encompasses a rim lined with six primary hydroxyl groups 206 from the monomeric glucose units, according to a first approach. These are generally the most reactive sites in the CD 104, and as such can be subject to several chemical manipulations. The other region is the secondary face 204, which encompasses a rim decorated with twelve secondary hydroxyl groups 208 from the glucose units, in a second approach. These secondary hydroxyl groups 208 are generally not as reactive as the primary hydroxyl groups 206.

One of the most useful reactions on the primary face 202 of the CD 104 is monotosylation, which allows for the activation of one of the six primary hydroxyl groups 206 for nucleophilic displacement, as shown in FIG. 3A, according to one embodiment. The range of nucleophiles that may be utilized for such displacement is vast, from small azides and thiols to alcohols and amines, among others, as would be known to one of skill in the art.

According to one embodiment, primary face 202 modification of a CD 104 involving up to two hydroxyl groups 206 may be performed with a high degree of precision via ditosylation, particularly when making use of reagents designed for this purpose, as shown in FIG. 3B.

Figure 3C:
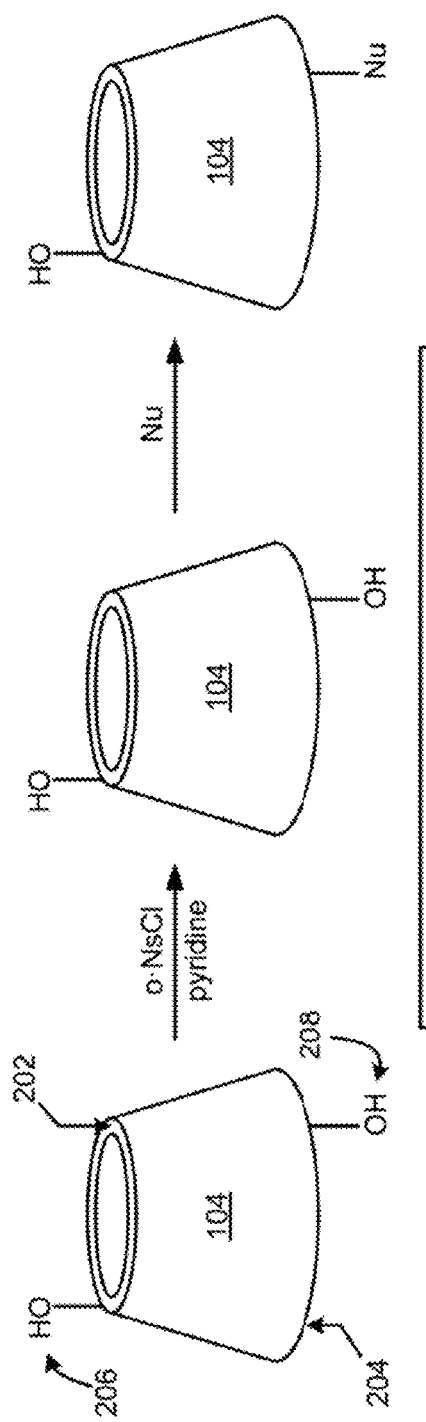
FIG. 3C shows chemical remodeling of cyclodextrin, according to one embodiment.

The second region of the CD 104 is known as its secondary face 204 and includes the twelve secondary hydroxyl groups 208 (C2 and C3) of the monomeric glucose units comprising the macromolecule, as shown in FIG. 2. The secondary hydroxyl groups 208 are generally less reactive than the primary hydroxyl groups 206, but they may be selectively modified by using an alkylating agent that gets encapsulated in the CD 104 cavity 210, thus allowing the secondary hydroxyl groups 208 to preferentially react with this reagent mainly as a result of proximity, in some approaches. As shown in FIG. 3C, one of these reagents is o-Nosyl chloride, which reacts preferentially with the C2-hydroxyl groups in the secondary face 204 of a CD 104, leaving the primary hydroxyl groups 206 and even the C3-hydroxyl groups of the secondary hydroxyl groups 208 untouched, as shown in one embodiment.

Figure 3D:
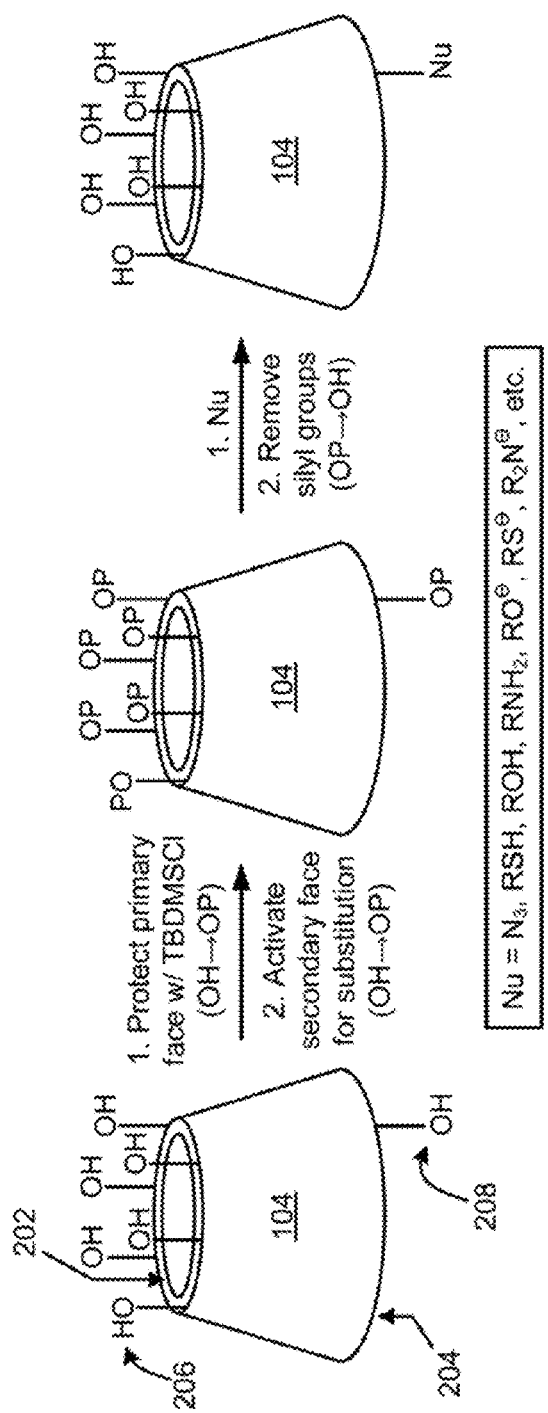
FIG. 3D shows chemical remodeling of cyclodextrin, according to one embodiment.

Additionally, if derivatization of only the secondary hydroxyl groups 208 is desired, the entire primary face 202 of the CD 104 may be capped with tertbutyldimethylsilyl chloride (TBDMSCl) to form a hexasilylated CD, as shown in FIG. 3D. With all the primary hydroxyl groups 206 temporarily blocked, the secondary face 204 may be modified as desired, and then the primary face 202 may be unmasked by removing the silyl protecting groups, such as with acid, fluoride ions, etc. In FIGS. 3A-3D, the modifying group may be any desired group as would be known to one of skill in the art, such as $N_3$, RSH, ROH, $RNH_2$, $RO^\ominus$, $RS^\ominus$, $R_2N^\ominus$, etc., where R may be any additional group as would be known to one of skill in the art, such as any organic moieties.

The chemical remodeling of a CD 104 is shown according to various embodiments in FIGS. 3A-3D. Of course, additional and/or altered modifications are also possible, in addition to or in place of those described in FIGS. 3A-3D. For example, the primary face 202 may be modified via monotosylation as shown in FIG. 3A, ditosylation as shown in FIG. 3B, etc., followed by nucleophilic displacement, in some approaches. The secondary face 204 may be modified using specific reagents such as nosyl chloride followed by substitution as shown in FIG. 3C, by making use of a more lengthy route involving the capping of the primary face 202 leaving the secondary face 204 available for the desired modification as shown in FIG. 3D, along with many other possible routes in other approaches. Removal of the protective groups at the primary face 202 after the secondary face 204 modification leads to the selectively functionalized CD 104, in one embodiment.

Once the modified metal nanoparticles are synthesized, they may be placed on a substrate, e.g., silicon wafer, glass slide, aerogel matrix, etc., according to some embodiments. These substrates with the modified metal nanoparticles may be used to detect and identify explosives by SERS, in preferred embodiments, along with the detection of various analytes of interest, in other embodiments.

Figure 4:
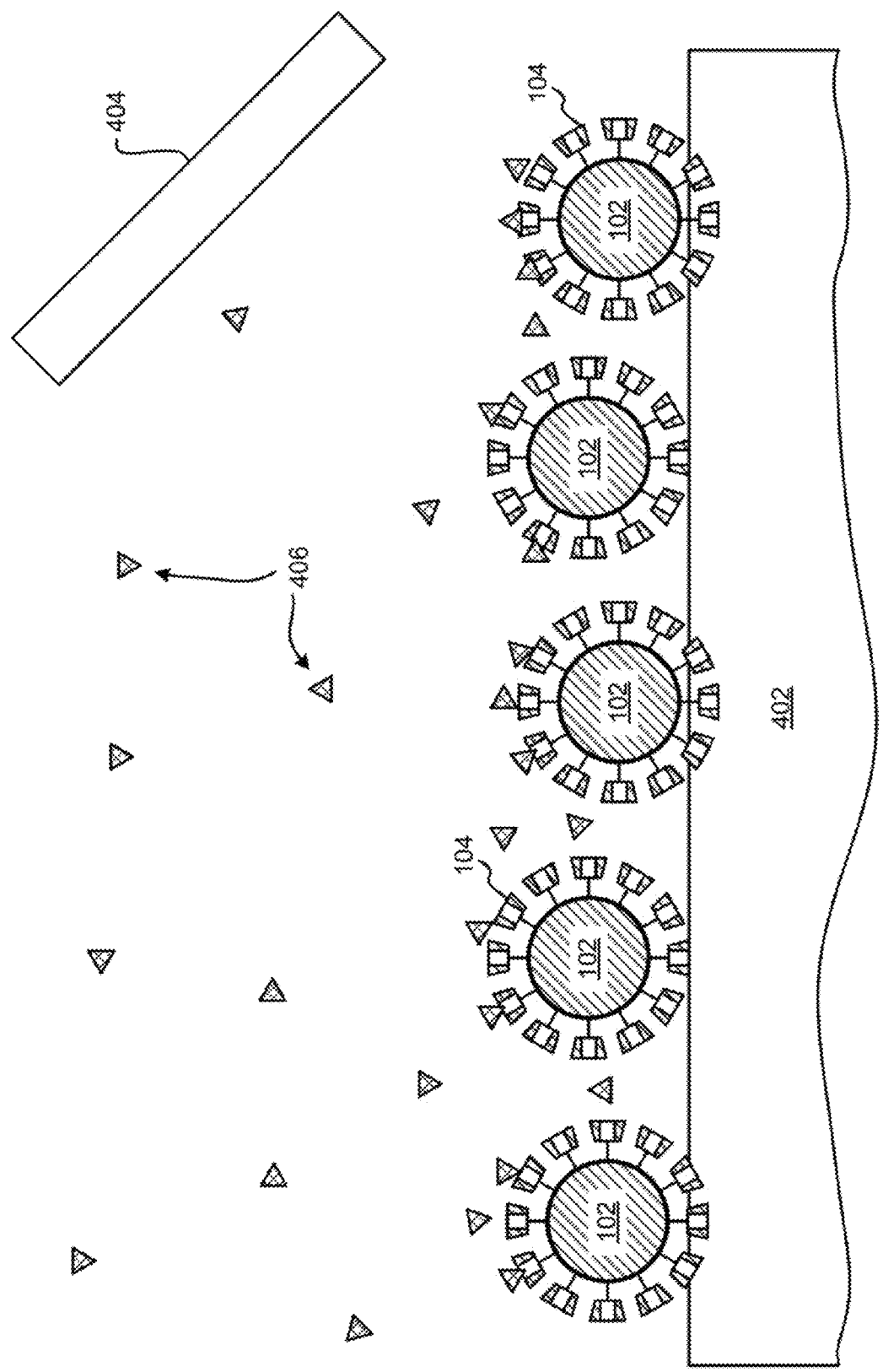
FIG. 4 is a simplified schematic of a Surface Enhanced Raman Spectroscopy (SERS) system, according to one embodiment.

Referring to FIG. 4, according to one embodiment, a system 400 includes a plurality of metal nanoparticles 102 functionalized with a plurality of organic molecules 104 tethered thereto. The plurality of organic molecules 104 preferentially interact with one or more analytes 406 when placed in proximity therewith. For example, the organic molecules 104 may be selected such that they bind to, attract, capture, etc., an analyte 406 of interest. Some exemplary analytes 406 include, but are not limited to, energetic compounds and/or materials, such as trinitrotoluene (TNT), tetrahexamine tetranitramine (HMX), cyclotrimethylenetrinitramine (RDX), pentaerythritol tetranitrate (PETN), trinitrophenylmethylnitramine (Tetryl), peroxides, etc.

In a further embodiment, the system 400 may include a substrate 402. The plurality of metal nanoparticles 102 may be attached to the substrate 402 through any mechanism as would be known to one of skill in the art, such as being bonded to the substrate 402, adhered to the substrate 402, attracted to the substrate 402, etc. The substrate 402 may be one of: silicon, glass, an aerogel having an inorganic matrix, and an aerogel having an organic matrix, among many other substances. The substrate 402 may also be a mixture of one or more materials.

In some embodiments, the metal nanoparticles 102 may have a mean diameter of between about 5 nm and about 100 nm, such as between about 20 nm and about 50 nm, between about 25 nm and about 40 nm, between about 5 nm and about 15 nm, etc.

In further approaches, the system 400 may include a Raman probe 404 for detecting the presence of the one or more analytes 406 interacting with the organic molecules 104.

In a preferred embodiment, the plurality of organic molecules 104 may comprise molecules of cyclodextrin, as shown in FIG. 4.

In this embodiment, as shown in FIGS. 1B, 3A-3D, the cyclodextrin molecules may be chemically modified at a primary hydroxyl moiety 206 to tether to a surface of the plurality of metal nanoparticles 102 via a chemical handle 108. Also, the chemical handle 108 may be at least one of: a thiol functionality and an amine functionality, in some approaches.

Also in this embodiment, the plurality of cyclodextrin molecules may include at least one modifying group on a primary face 202 in place of one or more primary hydroxyl groups 206. Further, the modifying groups may be selected from a group including: $N_3$, RSH, ROH, $RNH_2$, $RO^\ominus$, $RS^\ominus$, and $R_2N^\ominus$, wherein R is a carbon containing group known in the art, any modifying group or portion thereof, etc.

In more embodiments, the plurality of cyclodextrin molecules may include at least one modifying group on a secondary face 204 in place of one or more secondary hydroxyl groups 208. Further, the modifying groups may be selected from a group including: $N_3$, RSH, ROH, $RNH_2$, $RO^\ominus$, $RS^\ominus$, and $R_2N^\ominus$, wherein R is a carbon containing group known in the art, any modifying group or portion thereof, etc.

In more approaches, the plurality of cyclodextrin molecules may include one or more modifying groups on a primary face 202 in place of one or more primary hydroxyl groups 206 and one or more modifying groups on a secondary face 204 in place of one or more secondary hydroxyl groups 208. Further, the modifying groups may be selected from a group including: $N_3$, RSH, ROH, $RNH_2$, $RO^\ominus$, $RS^\ominus$, and $R_2N^\ominus$, wherein R is a carbon containing group known in the art, any modifying group or portion thereof, etc.

Figure 5:
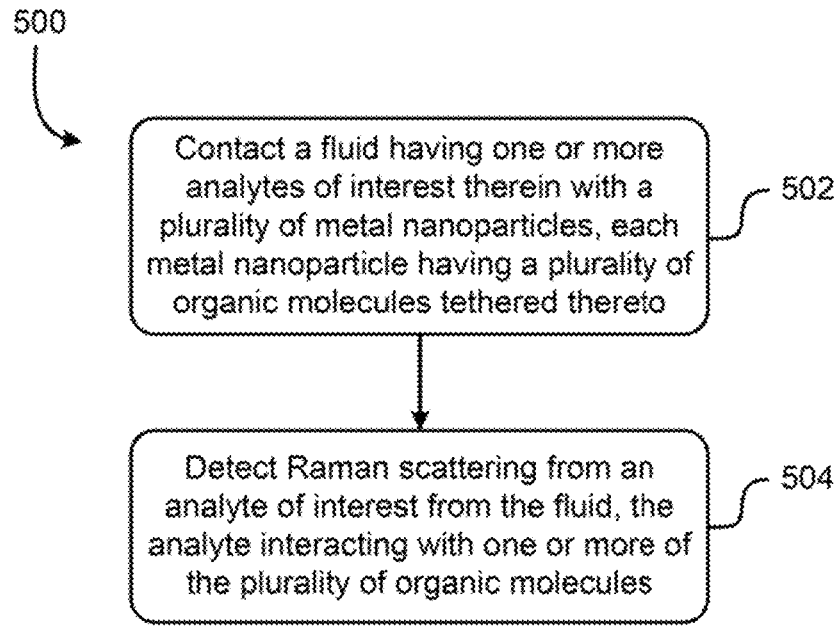
FIG. 5 is a flowchart of a method, according to one embodiment.

Now referring to FIG. 5, a method 500 for detecting analytes is shown according to one embodiment. The method 500 may be performed in any desired environment, and may include embodiments and approaches described in FIGS. 1A-4, according to various embodiments.

In operation 502, a fluid having one or more analytes of interest therein is contacted with a plurality of metal nanoparticles, each metal nanoparticle having a plurality of organic molecules tethered thereto. The fluid may be a liquid, a gas, a vapor, a suspension, etc., as would be known to one of skill in the art. The analytes may be energetic materials, such as explosives, etc., as described above; toxins; carcinogens; etc.

In operation 504, Raman scattering from an analyte of interest is detected from the fluid. The analyte interacts with one or more of the plurality of organic molecules, for example, by binding to, being attracted by, being captured by an organic molecule, etc.

In one approach, the plurality of metal nanoparticles may be attached to a substrate through any mechanism as would be known to one of skill in the art. The substrate may comprise one of: silicon, glass, an aerogel having an inorganic or organic matrix, or one of many other possible materials.

Figure 6:
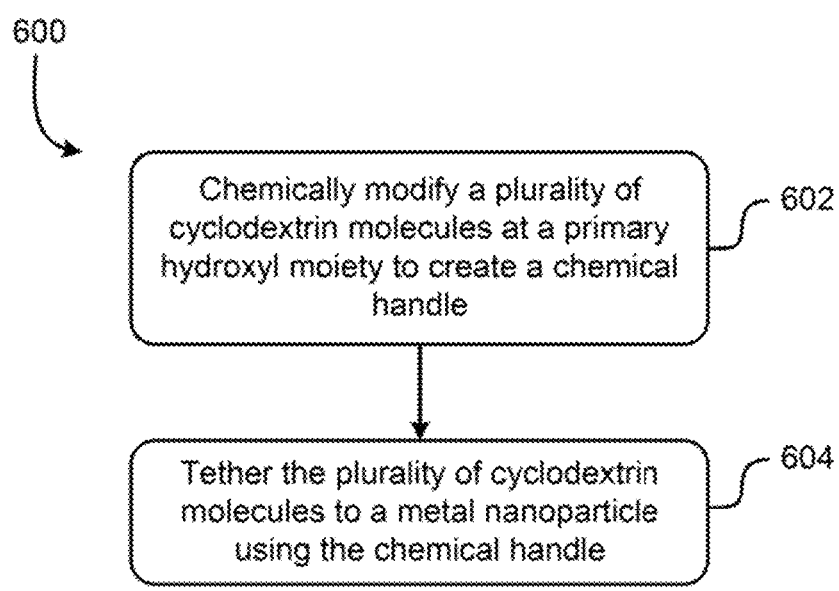
FIG. 6 is a flowchart of a method, according to one embodiment.

Now referring to FIG. 6, a method 600 is described according to one embodiment. The method 600 may be performed in any desired environment, and may include embodiments and approaches described in FIGS. 1A-4, according to various embodiments.

In operation 602, a plurality of cyclodextrin molecules are chemically modified at a primary hydroxyl moiety to create a chemical handle In operation 604, the plurality of cyclodextrin molecules are tethered to a metal nanoparticle using the chemical handle.

In one embodiment, the chemical handle may be at least one of: a thiol functionality and an amine functionality, among many other possible handles.

In another embodiment, the method 600 may include attaching a plurality of the metal nanoparticles having cyclodextrin molecules tethered thereto to a substrate. Any method of attaching the metal nanoparticles to the substrate may be used, as would be known to one of skill in the art. In a further embodiment, the substrate may be selected from a group including: silicon, silicon compounds, glass, and inorganic or organic aerogels, among many other possible materials.

In one approach, the method 600 may include chemically modifying the plurality of cyclodextrin molecules on a primary face via monotosylation of at least one primary hydroxyl group followed by nucleophilic displacement with an appropriate modifying group.

In one embodiment, the method 600 may include chemically modifying the plurality of cyclodextrin molecules on a primary face via ditosylation of at least two primary hydroxyl groups followed by nucleophilic displacement with appropriate modifying groups.

In another approach, the method 600 may include chemically modifying the plurality of cyclodextrin molecules on a secondary face via alkylation with an alkylating agent which becomes trapped in a cavity of the cyclodextrin molecule causing preferential reacting with one or more secondary hydroxyl groups.

In another embodiment, the method 600 may include chemically modifying the plurality of cyclodextrin molecules on a secondary face by capping a primary face with tertbutyldimethylsilyl chloride (TBDMSCl) to form hexasilylated cyclodextrin, followed by nucleophilic displacement of one or more secondary hydroxyl groups with an appropriate modifying group.

Figure 7:
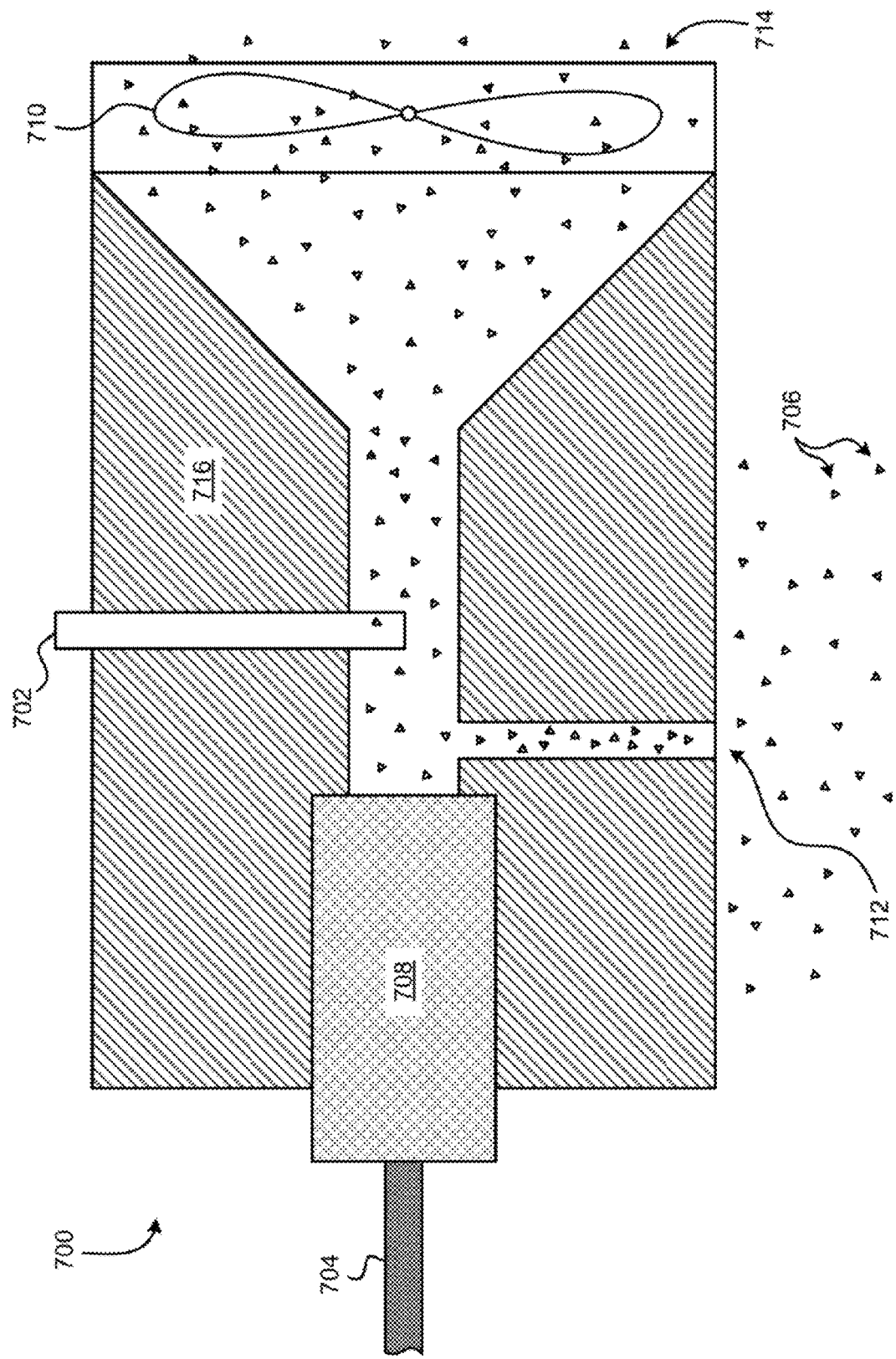
FIG. 7 is a SERS system, according to one embodiment.

Now referring to FIG. 7, a SERS system 700 is shown according to one embodiment. Of course, modifications, changes, alterations, etc., to this system are possible, and this exemplary embodiment is not meant to be limiting on the application or use of any embodiments described herein. The system 700 may include an adaptor sleeve 716 which may act to "focus" analytes 706 towards the SERS substrate 702, in some embodiments. Also, the sleeve 716 may slide over a Raman probe 708, which may be a fiber-optic Raman probe and may be connected to a fiber-optic cable 704 for coupling to a laser and to a spectrograph for reading reflections of the laser off the SERS substrate 702, and any analytes 706 located there. The vapor flows through the inlet 712, through the inner chamber of the sleeve 716, past the SERS substrate 702, and then out the outlet 714. Additionally, a fan 710 may be used to draw the vapor, including analytes 706 therein, through the sleeve 716. In addition, the SERS substrate 702, which may include any of the embodiments described herein for more effectively detecting analytes 706 of interest, is positioned at the focal point of the Raman probe 708 and partially blocks the air flow through the sleeve 716, creating turbulent flow at the substrate 702 face, according to one embodiment.

While various embodiments have been described above, it should be understood that they have been presented by way of example only, and not limitation. Thus, the breadth and scope of a preferred embodiment should not be limited by any of the above-described exemplary embodiments, but should be defined only in accordance with the following claims and their equivalents.

What is claimed is:

1. A system, comprising:
   one or more analytes; and
   a plurality of metal nanoparticles functionalized with a plurality of organic molecules tethered thereto, each organic molecule having a primary face and a secondary face,
   wherein the plurality of organic molecules preferentially interact with the one or more analytes when placed in proximity therewith,
   wherein the plurality of organic molecules comprise one or more of:
      one or more modifying groups on the primary face in place of one or more primary hydroxyl groups; and
      one or more modifying groups on the secondary face in place of one or more secondary hydroxyl groups,
   wherein at least one of the one or more analytes is an energetic compound selected from a group consisting of: trinitrotoluene (TNT), tetrahexamine tetranitramine (HMX), cyclotrimethylenetrinitramine (RDX), pentaerythritol tetranitrate (PETN), 2,4,6-trinitrophenylmethylnitramine (Tetryl), and peroxides.

2. The system of claim 1, wherein at least some of the plurality of organic molecules are molecules of modified cyclodextrin.

3. The system of claim 2, wherein the cyclodextrin molecules are chemically modified at a primary hydroxyl moiety to tether to a surface of the plurality of metal nanoparticles via a chemical handle.

4. The system of claim 3, wherein the chemical handle is at least one of: a thiol functionality and an amine functionality.

5. The system of claim 2, wherein the plurality of cyclodextrin molecules include at least one modifying group on a primary face in place of one or more primary hydroxyl groups.

6. The system of claim 5, wherein the modifying groups are selected from a group consisting of: $N_3$, RSH, ROH, $RNH_2$, $RO^\ominus$, $RS^\ominus$, and $R_2N^\ominus$, wherein R is any carbon containing group, or any modifying group.

7. The system of claim 2, wherein the plurality of cyclodextrin molecules include at least one modifying group on a secondary face in place of one or more secondary hydroxyl groups.

8. The system of claim 7, wherein the modifying groups are selected from a group consisting of: $N_3$, RSH, ROH, $RNH_2$, $RO^\ominus$, $RS^\ominus$, and $R_2N^\ominus$, wherein R is any carbon containing group, or any modifying group.

9. The system of claim 2, wherein the plurality of cyclodextrin molecules include one or more modifying groups on a primary face in place of one or more primary hydroxyl groups and one or more modifying groups on a secondary face in place of one or more secondary hydroxyl groups.

10. The system of claim 9, wherein the modifying groups are selected from a group consisting of: $N_3$, RSH, ROH, $RNH_2$, $RO^\ominus$, $RS^\ominus$, and $R_2N^\ominus$, wherein R is any carbon containing group, or any modifying group.

11. The system of claim 4, wherein the chemical handle is a functional group selected from a group consisting of: of a thiol (—SH) functional group; and an amine (—$NH_2$) functional group.

12. The system of claim 1, wherein the plurality of organic molecules comprise molecules of modified cyclodextrin,
   wherein the cyclodextrin molecules are chemically modified at a primary hydroxyl moiety to tether to a surface of the plurality of metal nanoparticles via a chemical handle, and
   wherein the chemical handle is an amine functionality.

13. The system of claim 1, wherein the metal nanoparticles comprise one or more of silver nanoparticles and platinum nanoparticles.

14. The system of claim 1, further comprising a substrate, wherein the plurality of metal nanoparticles are attached to the substrate, and
   wherein the substrate comprises one of: silicon, glass, an aerogel having an inorganic matrix, and an aerogel having an organic matrix.

15. The system of claim 1, wherein the metal nanoparticles have a mean diameter of between about 5 nm and about 100 nm.

16. The system of claim 1, further comprising a Raman probe for detecting the presence of the one or more analytes interacting with the organic molecules.

17. The system of claim 1, further comprising:
   a housing;
   an inlet;
   an outlet;
   a fan configured to draw vapor through the housing from the inlet toward the outlet;
   a substrate;
   a Raman probe for detecting a presence of the one or more analytes in the vapor; and
   a fibre optic cable adapted to couple a laser to a spectrograph.

18. The system of claim 1, further comprising:
   a housing;
   an inlet;
   an outlet;
   a fan configured to draw vapor through the housing from the inlet toward the outlet;
   a surface-enhanced Raman Spectroscopy (SERS) substrate comprising an aerogel having an organic matrix;

a Raman probe for detecting a presence of the one or more analytes in the vapor; and a fibre optic cable adapted to couple a laser to a spectrograph, wherein the plurality of metal nanoparticles are attached to the substrate;

wherein the chemical handle consists of a functional group selected from a group consisting of: of a thiol (—SH) functional group; and an amine (—NH$_2$) functional group, wherein the metal nanoparticles have a mean diameter of between about 5 nm and about 100 nm, wherein the metal nanoparticles comprise one or more of silver nanoparticles and platinum nanoparticles, and wherein the modifying groups are selected from a group consisting of: N$_3$, RSH, ROH, RNH$_2$, RO$^\ominus$, RS$^\ominus$, and R$_2$N$^\ominus$, wherein R is any carbon containing group, or any modifying group.

19. A method for detecting one or more energetic analytes, the method comprising:

contacting a fluid having one or more of the energetic analytes of interest therein with a plurality of metal nanoparticles, each metal nanoparticle having at least one modified cyclodextrin molecule tethered thereto; and detecting Raman scattering from an energetic analyte of interest from the fluid, the energetic analyte of interest interacting with one or more of the modified cyclodextrin molecules via a modifying group present on one or more of:

a primary face of the modified cyclodextrin molecule; and a secondary face of the modified cyclodextrin molecule, wherein each of the modified cyclodextrin molecules comprises one or more of:

one or more modifying groups on the primary face in place of one or more primary hydroxyl groups; and one or more modifying groups on the secondary face in place of one or more secondary hydroxyl groups, wherein the modifying group comprises a functional group selected from N$_3$, RSH, ROH, RNH$_2$, RO$^\ominus$, RS$^\ominus$, and R$_2$N$^\ominus$, wherein R is any carbon containing group, or any modifying group, and wherein the energetic analyte of interest is selected from a group consisting of: trinitrotoluene (TNT), tetrahexamine tetranitramine (HMX), cyclotrimethylenetrinitramine (RDX), pentaerythritol tetranitrate (PETN), 2,4,6-trinitrophenylmethylnitramine (Tetryl), and peroxides.

20. The method of claim 19, wherein the plurality of metal nanoparticles are attached to a substrate comprising one of: an aerogel having an inorganic matrix, and an aerogel having an organic matrix.

* * * * *